United States Patent [19]
Pope et al.

[11] Patent Number: 6,010,533
[45] Date of Patent: Jan. 4, 2000

[54] PROSTHETIC JOINT WITH DIAMOND COATED INTERFACES

[75] Inventors: Bill J. Pope; Richard M. Garrick, both of Provo, Utah

[73] Assignee: Diamicron, Inc., Orem, Utah

[21] Appl. No.: 08/844,395

[22] Filed: Apr. 18, 1997

Related U.S. Application Data

[63] Continuation of application No. 08/631,887, Apr. 16, 1996, Pat. No. 5,645,601.
[51] Int. Cl.[7] ...................................................... A61F 2/34
[52] U.S. Cl. ................................................................ 623/18
[58] Field of Search ........................... 359/642; 156/613, 156/614; 428/336; 623/16, 18, 20, 22, 66

[56] References Cited

U.S. PATENT DOCUMENTS 5,358,529  10/1994  Davidson .................................. 623/20

*Primary Examiner*—David J. Isabella
*Attorney, Agent, or Firm*—Calvin Thorpe; Daniel McCarthy

[57] ABSTRACT

A prosthetic joint with polycrystalline diamond compact coated interfaces and a method for making the same are disclosed. The prosthetic joint has a diamond layer formed on at least one of the interacting, load-bearing surfaces of the joint. The diamond layer adds resistance to damage from impacts and, when polished, gives the joint a low coefficient of friction, thereby increasing the life of the joint. In accordance with one aspect of the invention, the diamond layer is formed of polycrystalline diamond compact having a common diamond particle diameter of less than 1 micron to further reduce friction.

7 Claims, 2 Drawing Sheets

PROSTHETIC JOINT WITH DIAMOND COATED INTERFACES

This application is a continuation of application Ser. No. 08/631,877, filed on Apr. 16, 1996, now U.S. Pat. No. 5,645,601.

BACKGROUND OF INVENTION

The present invention relates to a prosthetic joint, and in particular to a prosthetic joint having diamond-coated load-bearing surfaces to thereby reduce friction and increase the useful life of the joint.

The use of prosthetic joints to replace joints which have either been worn out or damaged in an accident has become commonplace. The use of prosthetic joints has allowed many people with severe joint problems to return to activity, and enjoy a relatively normal lifestyle. While prosthetic joints have been used in numerous applications, the most common are those used to replace knees and hips which have either worn out, been fractured, or otherwise been damaged The primary problem with prosthetic joints is that the joints eventually erode and must be replaced. This erosion is caused, in large part, by the forces of impact and friction routinely encountered by the load-bearing surfaces of the prosthetic joint. As the joint is repeatedly used, the ball and socket (in the case of a hip prosthesis) wear against each other. The impact and friction forces eventually cause pieces of the load-bearing surfaces to spall and float about the joint. This debris initiates a hystiocytic reaction in which the body's immune system is activated and releases enzymes to dissolve the particles. However, because the debris is usually relatively hard material, such as metal or polycarbon compounds, the enzymes usually fail to dissolve the debris, or take a considerable amount of time to do so. To further complicate matters, the enzymes react with the bone supporting the prosthetic joint. The enzymes weaken or dissolve the bone. This condition causes osteolysis or weakening of the bone, therefor weakening attachment to the bone and making it difficult to replace the prosthetic joint when the bearing surfaces have eroded to such a point that the joint should be replaced. Osteolysis decreases the lifetime of the replacement prosthetic joint, and eventually renders the bone unusable.

Thus, there is a need for a prosthetic joint that will function the remainder of the life of the recipient without osteolysis. The present invention accomplishes this by introducing long wearing, low friction, diamond-coated bearing surfaces, thereby decreasing the amount of debris eroded into the joint, so as to extend the life of the joint.

SUMMARY OF TEE INVENTION

It is an object of the present invention to provide a prosthetic joint for replacement of faulty natural joints which significantly decreases load-bearing surface erosion and debris.

It is an additional object of the present invention to provide a prosthetic joint which has load-bearing surfaces of sufficient strength to obviate the need for repetitive replacement of the joint.

It is yet another object of the present invention to provide a prosthetic joint which has a low coefficient of friction between its load-bearing surfaces.

The above and other objects of the invention are realized in a prosthetic joint having a thin layer of diamond bonded to at least one of the bearing surfaces of the joint. The diamond compact is affixed to the bearing surfaces and processed in such a way as to give the diamond coating a high luster and a low coefficient of friction.

In accordance with one aspect of the invention, the diamond layer is formed from polycrystalline diamond compact having a diamond particle diameter of between one nanometers and ten microns, to thereby further reduce the coefficient of friction between the bearing surfaces.

BRIEF DESCRIPTION OF THE DRAWINGS

The above, and other objects, features and advantages of the invention, will become apparent from the following detailed description presented in conjunction with the accompanying drawings, in which.

DETAILED DESCRIPTION

Figure 1:
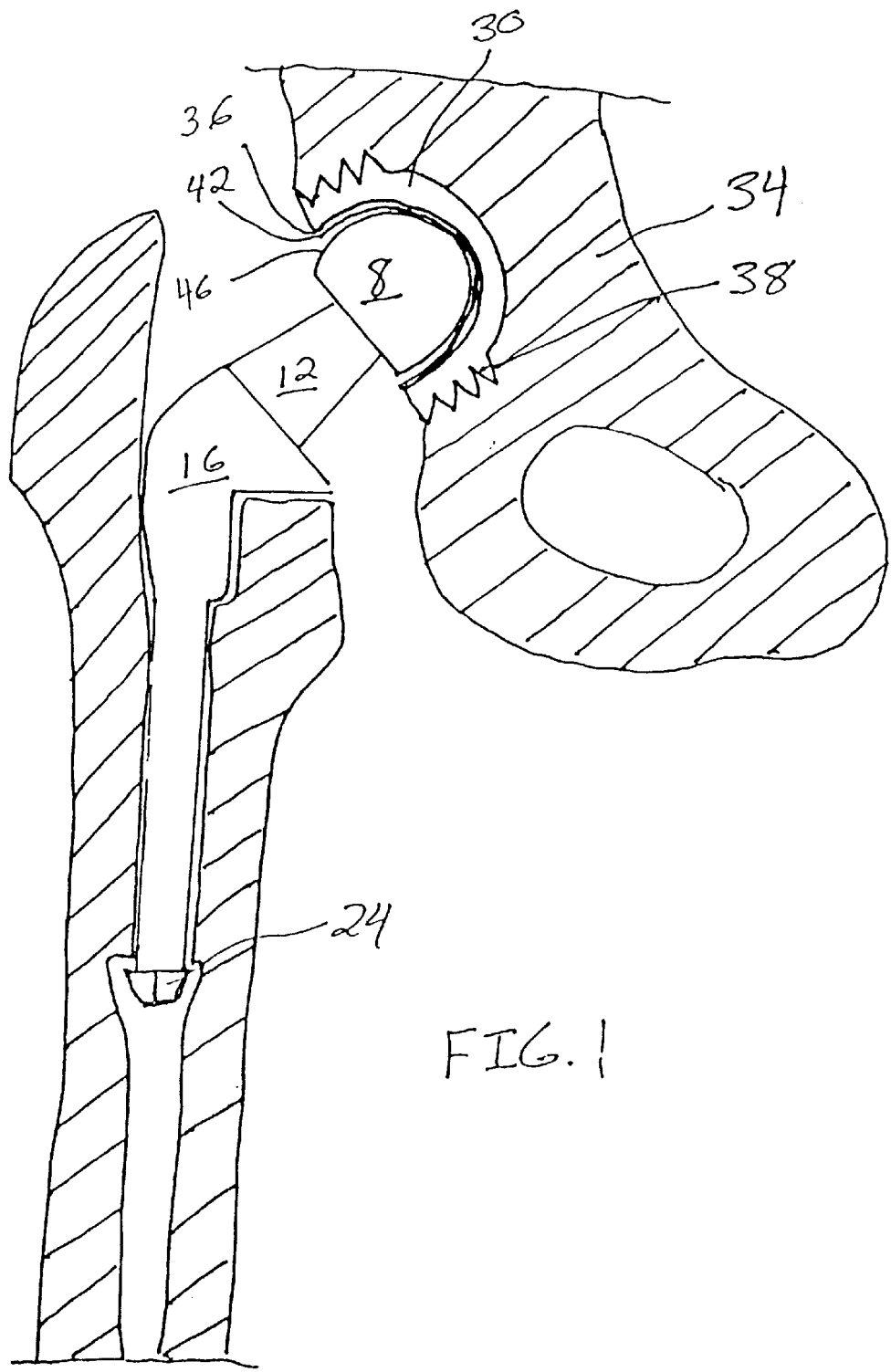
FIG. 1 shows a side cross-sectional view of a prosthetic hip joint such as those commonly mounted in the hip of a human body.

Reference will now be made to the drawings in which the various elements of the present invention will be discussed using the human prosthetic hip joint as an example, using numeral designations so as to enable one skilled in the art to make and use the invention for other types of prosthetic joints. Referring to FIG. 1 there is shown a prosthetic hip joint, generally indicated at 4. The prosthetic hip joint 4 consists of a ball 8 which is connected by a stem 12 to an anchor 16. Typically, the ball 8 is metal and is mounted to a metal stem 12 by a Morse taper. However, the ball 8 may be made of a durable, biocompatible material. Additionally, the ball may be attached to the stem 12 by a variety of means.

The anchor 16 is held in place in the femur by bone adhesive, such as bone cement using a cement mantle 24, friction or a threaded mechanism which extends down into the center of the femur. Recently, there has been increased use of porous surfaces along the outside of the anchor 16 which allows the bone to grow into the exterior surface of the anchor, thereby holding the anchor in place.

A cup shaped socket 30 is anchored in the pelvis 34 by a knurled or threaded exterior 38. The ball 8 is positioned adjacent the concave load-bearing surface 36 of the socket 30 so as to permit rotation, simulating the movement of the natural hip joint. As shown in FIG. 1, a high molecular weight polymer liner 42 is disposed within the socket 30 so as to decrease friction between the ball 8 and the socket 30, thereby increasing the life of the joint 4. The outer surface of the ball 8 is generally referred to as the load-bearing area 46 of the ball, as this area interfaces with the load-bearing surface 36 of the socket 30 and allows the joint 4 to rotate.

As was discussed in the background section, in such an arrangement wear during use produces small debris fragments as the load-bearing surfaces of the ball 8 and the socket 30 or liner 42 rub against each other. Eventually the enzymes activated to dissolve the debris will weaken the bones (20 and 34) housing the anchor 16 and the socket 30, making it difficult to replace the prosthetic joint.

Figure 2:
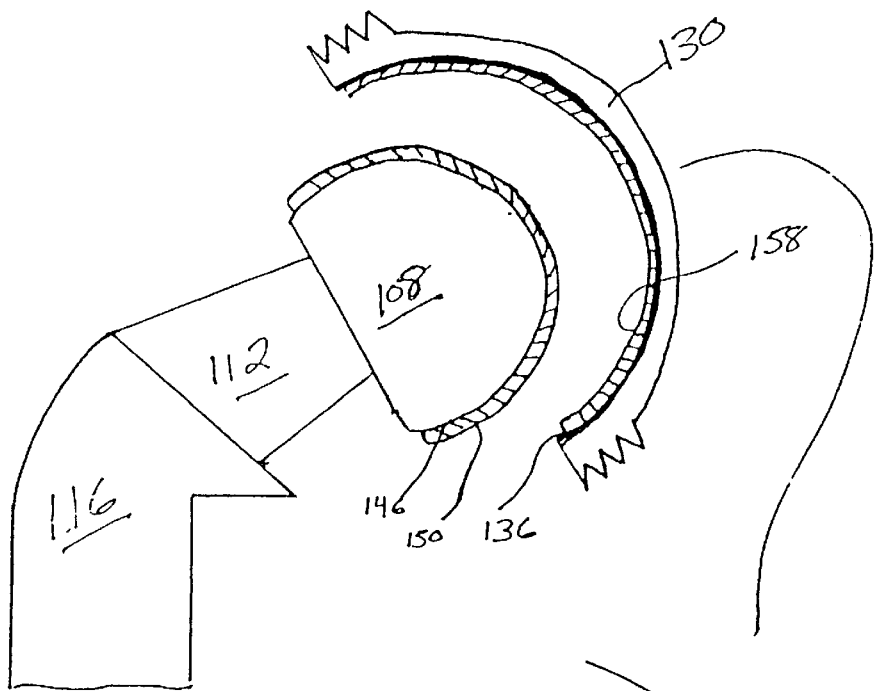
FIG. 2 shows an enlarged side cross-sectional view of one embodiment of a prosthetic hip joint made in accordance with the principles of the present invention.
Figure 2A:
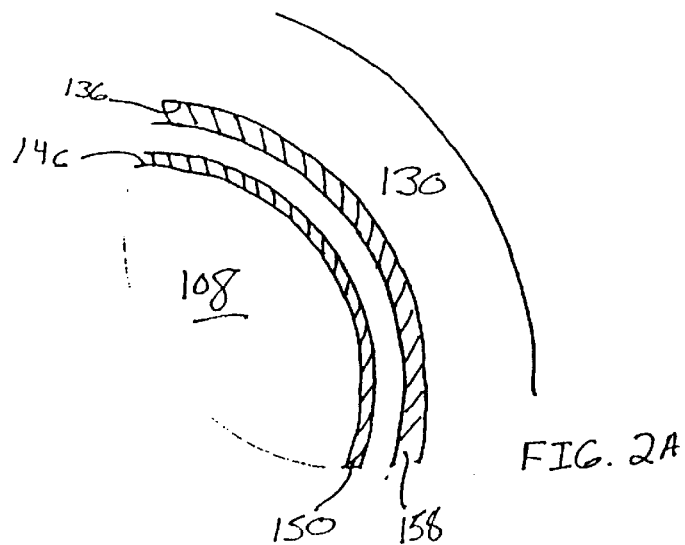
FIG. 2A shows a blow-up of the diamond layers disposed on the ball and socket of the present invention.

FIGS. 2 and 2A illustrate one embodiment of the present invention. FIG. 2 shows diamond-coated load-bearing surfaces forming a joint 104. The joint 104 shown includes a ball 108, stem 112, a fragmented view of the anchor 116 and a socket 130 similar to those shown in FIG. 1. In accordance with the principles of the present invention, the socket 130 and the ball 108 may still be made of durable metal. For example, the ball 108 and socket 130 could be made of titanium, cobalt-chrome alloys, or stainless steel. Such materials are well known in the prosthetic joint art, and have long been considered safe for such purposes. Those skilled in the art will also be able to apply the principles of the present invention to other hard materials such as polycarbon compounds, which may be used in prosthetic joints.

In accordance with the present invention it has been found that forming thin layers of polished diamond 150 and 158 on the load-bearing areas 146 and 136, both reduces debris, and significantly increases the life of the prosthetic joint. A blown-up view of the load-bearing surfaces 136 and 146 and the diamond layers 150 and 158 is shown in FIG. 2A. (In FIGS. 2 and 2A, the thickness of the diamond layers are exaggerated to make them visible. The actual thickness is between less than 1000 microns, and may be less than 1 micron). These polished diamond layers, 150 and 158, have a very low coefficient of friction, and are very hard, thereby effectively eliminating debris from interfering with the joint. While a conventional prosthetic joint has a typical life of approximately 10 years, by placing a diamond coating on the load bearing surfaces, the life of the joint can be increased significantly. For many joints it may altogether obviate the necessity of periodically replacing the joint.

The diamond layers 150 and 158 are typically formed by bonding diamond compact to the load-bearing surface (146 or 136) by sintering at high temperature and high pressure, high temperature laser application, electroplating, chemical vapor deposition, forming a matrix with high molecular weight polyethylene or by other methods which are known in the art. Once the diamond layers 150 and 158 have been applied to the ball 108 and/or socket 130, the diamond surface is polished to a Ra value between 0.10 and 0.01 microns. The friction, and consequently the wear between surface layers 150 and 158, is extremely low, thereby increasing the life of the diamond-diamond joint 104 beyond that of the present art.

While shown in FIG. 2 as having diamond layers on both the ball 108 and socket 130, a single diamond layer, either the ball 108, or the socket 130 may have the diamond layer. However, the preferred embodiment is with diamond layers on each load-bearing surface of the joint 104. The two diamond layers 150 and 158 decrease the coefficient of friction between the two load-bearing surfaces 146 and 136 and decrease the likelihood of debris generated by movement of the joint 104.

Typically, polycrystalline diamond compact is formed using particles of diamond having a diameter of approximately one to one hundred microns. Use of such compact results in a prosthetic joint 104 which is more durable and less likely to erode. However, it has been found that a preferred layer 150 or 158 is formed by using polycrystalline diamond compact having a diamond particle diameter between one nanometer and one micron. The use of smaller diameter diamond particles increases the life of the prosthetic joint 104. This is so because the smaller diameter of the diamond particles makes them easier to polish to a fine surface, resulting in a lower coefficient of friction. Thus, there is a decrease in the amount of erosion debris, decreasing the risk of hystiocytic reactions and increasing the useful life of the joint.

As will be apparent to those skilled in the art, the polycrystalline diamond layer could be bonded to one of the load-bearing surfaces by any satisfactory method, and to an opposing load-bearing surface by some other method. Those skilled in the art will recognize that other methods and materials may be used to form the joint.

It has long been known that polycrystalline materials can be bonded to substrates, such as cemented tungsten carbide and used on rock bits for oil and natural gas. The polycrystalline material is typically bonded to the substrate at pressures in excess of 50,000 atmospheres and temperatures in excess of 1,300° C. For more detailed descriptions of methods of applying polycrystalline compacts to a substrate, see U.S. Pat. Nos. 3,745,623; 3,767,371; 3,871,840; 3,841,852; 3,913,280; and 4,311,490.

Once the polycrystalline diamond compact has been applied to the load-bearing surfaces 146 and 136 of the prosthetic joint 48, it is polished to an Ra value of 0.1 to 0.01 microns by the use of concave and convex spherical diamond laps. The thin diamond layers 150 and 158, now disposed on the load-bearing surfaces 146 and 136, respectively, of the prosthetic joint 104, create a joint with surfaces which are resistant to high-impact loads and which have a low coefficient of friction. Thus, impacting the surfaces together and interaction between the surfaces by rotation of the ball 108 within the socket 130 will not lead to wear of the surfaces and generation of debris as has been the case with prior prosthetic joints.

In the manner described, a prosthetic joint with diamond-coated interfaces is provided. The joint utilizes a thin diamond layer on at least one of the load-bearing surfaces of the joint to decrease friction within the joint and decrease debris caused by erosion of the load-bearing surface. It is to be understood that the above-described arrangements are only illustrative of the application of the principals of the present invention Numerous modifications and alternate arrangements may be devised by those skilled in the art without departing from the spirit and scope of the invention. The appended claims are intended to cover such modifications and arrangements.

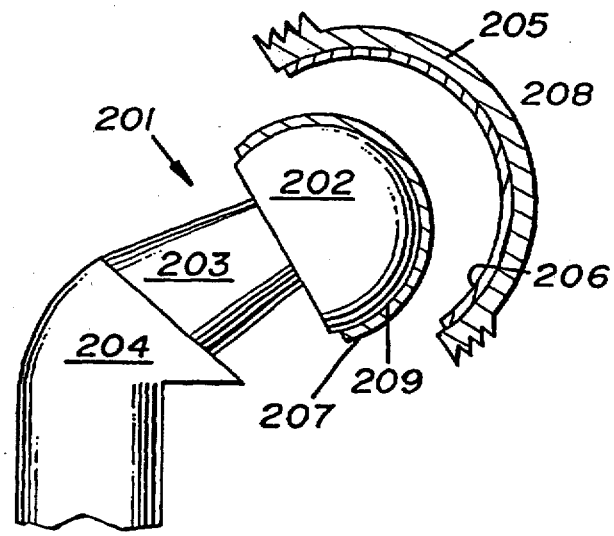

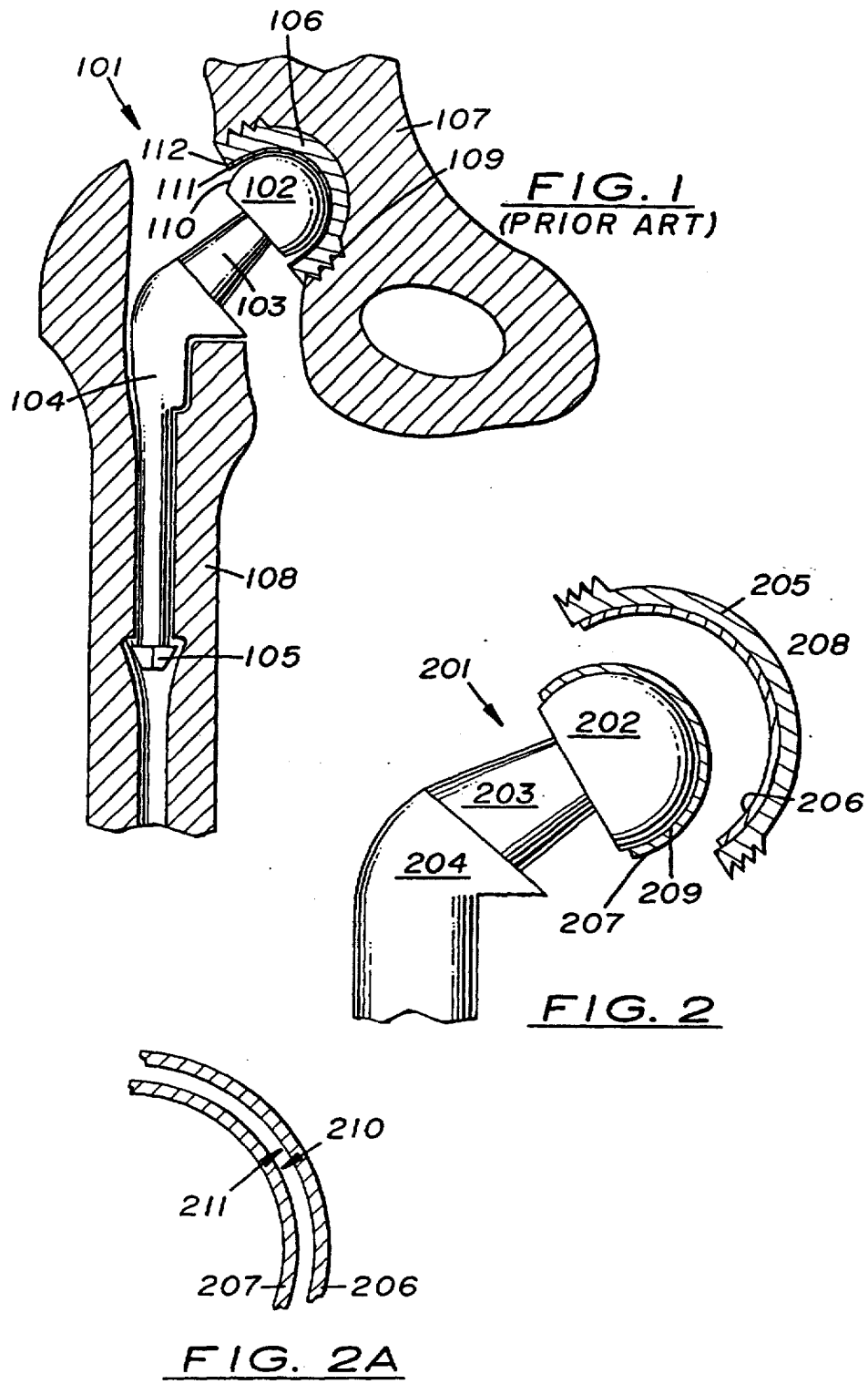

What is claimed is:

1. A method of making a prosthetic joint having load-bearing surfaces which interact to enable rotation of one of the load-bearing surfaces relative to the other, the method comprising the steps of:

(a) coating at least one of the load-bearing surfaces with a polycrystalline diamond compact; and (b) bonding the compact to said diamond-coated load-bearing surface to form a diamond layer over said diamond-coated load-bearing surface;

wherein step (b) comprises bonding a compact to a first of the load-bearing surfaces by using one of the group of processes consisting of a sintering process under high pressure and high temperature, a high temperature laser, chemical vapor deposition, electroplating and forming a matrix of high molecular weight polyethylene.

2. The method of claim 1, wherein step (a) comprises coating both load-bearing surfaces with a polycrystalline diamond compact to form a pair of diamond layers, each over a respective one of the load-bearing surfaces.

3. The method of claim 1, wherein step (a) comprises coating at least one of the load-bearing surfaces with a polycrystalline diamond compact having diamond particles with a common diameter of less than 100 microns.

4. The method of claim 1, wherein step (a) comprises coating at least one of the load-bearing surfaces with a polycrystalline diamond compact having diamond particles with a common diameter of less than 1 micron.

5. The method of claim 1, wherein step (a) comprises coating at least one of the load-bearing surfaces with a polycrystalline diamond compact having diamond particles with a common diameter of between about 1 nanometer and 1 micron.

6. The method of claim 1, further comprising the step of polishing the diamond layer to a high luster to thereby provide the diamond layer a low coefficient of friction.

7. The method of claim 6, wherein said polishing step comprises polishing the diamond layer to an Ra value of between 0.1 and 0.010 microns.

* * * * *

UNITED STATES PATENT AND TRADEMARK OFFICE
CERTIFICATE OF CORRECTION

PATENT NO. : 6,010,533  
DATED : January 4, 2000  
INVENTOR(S) : Pope et al.

Page 1 of 3

It is certified that error appears in the above-identified patent and that said Letters Patent is hereby corrected as shown below:

<u>Title page,</u>
Item [63] should read as follows:
-- Continuation of apllication serial no. 08/631,887, Apr. 16, 1996, Pat No. 5,645,601, which is a continuation of application serial no. 08/289,696, Aug. 12, 1994, abandoned. --

Title page, should appear as attached
Drawings figs should appear as per attached.

Signed and Sealed this

Twenty-ninth Day of January, 2002

Attest:

Attesting Officer

JAMES E. ROGAN
Director of the United States Patent and Trademark Office

United States Patent [19]

Pope et al.

[11] Patent Number: 6,010,533

[45] Date of Patent: Jan. 4, 2000

[54] PROSTHETIC JOINT WITH DIAMOND COATED INTERFACES

[75] Inventors: Bill J. Pope; Richard M. Garrick, both of Provo, Utah

[73] Assignee: Diamicron, Inc., Orem, Utah

[21] Appl. No.: 08/844,395

[22] Filed: Apr. 18, 1997

Related U.S. Application Data

[63] Continuation of application No. 08/631,887, Apr. 16, 1996, Pat. No. 5,645,601.
[51] Int. Cl.⁷ .................................................. A61F 2/34
[52] U.S. Cl. ........................................................ 623/18
[58] Field of Search ........................... 359/642; 156/613, 156/614; 428/336; 623/16, 18, 20, 22, 66

[56] References Cited

U.S. PATENT DOCUMENTS

5,358,529  10/1994  Davidson ................................. 623/20.

*Primary Examiner*—David J. Isabella
*Attorney, Agent, or Firm*—Calvin Thorpe; Daniel McCarthy

[57] ABSTRACT

A prosthetic joint with polycrystalline diamond compact coated interfaces and a method for making the same are disclosed. The prosthetic joint has a diamond layer formed on at least one of the interacting, load-bearing surfaces of the joint. The diamond layer adds resistance to damage from impacts and, when polished, gives the joint a low coefficient of friction, thereby increasing the life of the joint. In accordance with one aspect of the invention, the diamond layer is formed of polycrystalline diamond compact having a common diamond particle diameter of less than 1 micron to further reduce friction.

7 Claims, 2 Drawing Sheets